United States Patent [19]

O'Rourke et al.

[11] Patent Number: 5,402,508
[45] Date of Patent: Mar. 28, 1995

[54] FIBER OPTIC PROBE HAVING FIBERS WITH ENDFACES FORMED FOR IMPROVED COUPLING EFFICIENCY AND METHOD USING SAME

[75] Inventors: Patrick E. O'Rourke, Martinez, Ga.; Ronald R. Livingston, Aiken, S.C.

[73] Assignee: The United States of America as represented by the United States Department of Energy, Washington, D.C.

[21] Appl. No.: 56,390

[22] Filed: May 4, 1993

[51] Int. Cl.⁶ .................... G02B 6/06; H01J 5/16; G01L 1/24
[52] U.S. Cl. .................... 385/31; 385/12; 385/38; 385/85; 385/88; 385/115; 385/116; 385/133; 250/227.11; 250/227.14; 250/227.2; 250/577; 73/800
[58] Field of Search ............... 385/31, 38, 88, 85, 385/89, 133, 115, 116, 117, 120, 126, 12, 13, 15; 250/227.11, 227.2, 227.14, 227.18, 573, 577; 73/800

[56] References Cited

U.S. PATENT DOCUMENTS

| | | | |
|---|---|---|---|
| 4,038,650 | 7/1977 | Evans et al. | 385/12 X |
| 4,272,156 | 6/1981 | Ishibashi et al. | 385/117 |
| 4,468,567 | 8/1984 | Sasano et al. | 385/12 X |
| 4,573,761 | 3/1986 | McLachlan et al. | 385/115 X |
| 4,707,134 | 11/1987 | McLachlan et al. | 356/342 |
| 4,812,003 | 3/1989 | Dambach et al. | 385/12 X |
| 4,816,670 | 3/1989 | Kitamura et al. | 250/227.11 X |
| 4,914,284 | 4/1990 | Halldorsson et al. | 250/206.2 |
| 4,919,891 | 4/1990 | Yafuso et al. | 422/58 |
| 4,979,797 | 12/1990 | Nemeth | 385/12 X |
| 5,011,279 | 4/1991 | Auweter et al. | 385/15 X |
| 5,166,756 | 11/1992 | McGee et al. | 356/446 |

*Primary Examiner*—Brian Healy
*Attorney, Agent, or Firm*—Brian R. Tumm; Harold M. Dixon; William R. Moser

[57] ABSTRACT

A fiber optic probe for detecting scattered light, with transmitting and receiving fibers having slanted ends and bundled together to form a bevel within the tip of the probe. The probe comprises a housing with a transparent window across its tip for protecting the transmitting and receiving fibers held therein. The endfaces of the fibers are slanted, by cutting, polishing and the like, so that they lie in a plane that is not perpendicular to the longitudinal axis of the respective fiber. The fibers are held in the tip of the probe using an epoxy and oriented so that lines normal to the slanted endfaces are divergent with respect to one another. The epoxy, which is positioned substantially between the transmitting and receiving fibers, is tapered so that the transmitting fiber, the epoxy and the receiving fiber form a bevel of not more than 20 degrees. The angled fiber endfaces cause directing of the light cones toward each other, resulting in improved light coupling efficiency. A light absorber, such as carbon black, is contained in the epoxy to reduce crosstalk between the transmitting and receiving fibers.

17 Claims, 1 Drawing Sheet

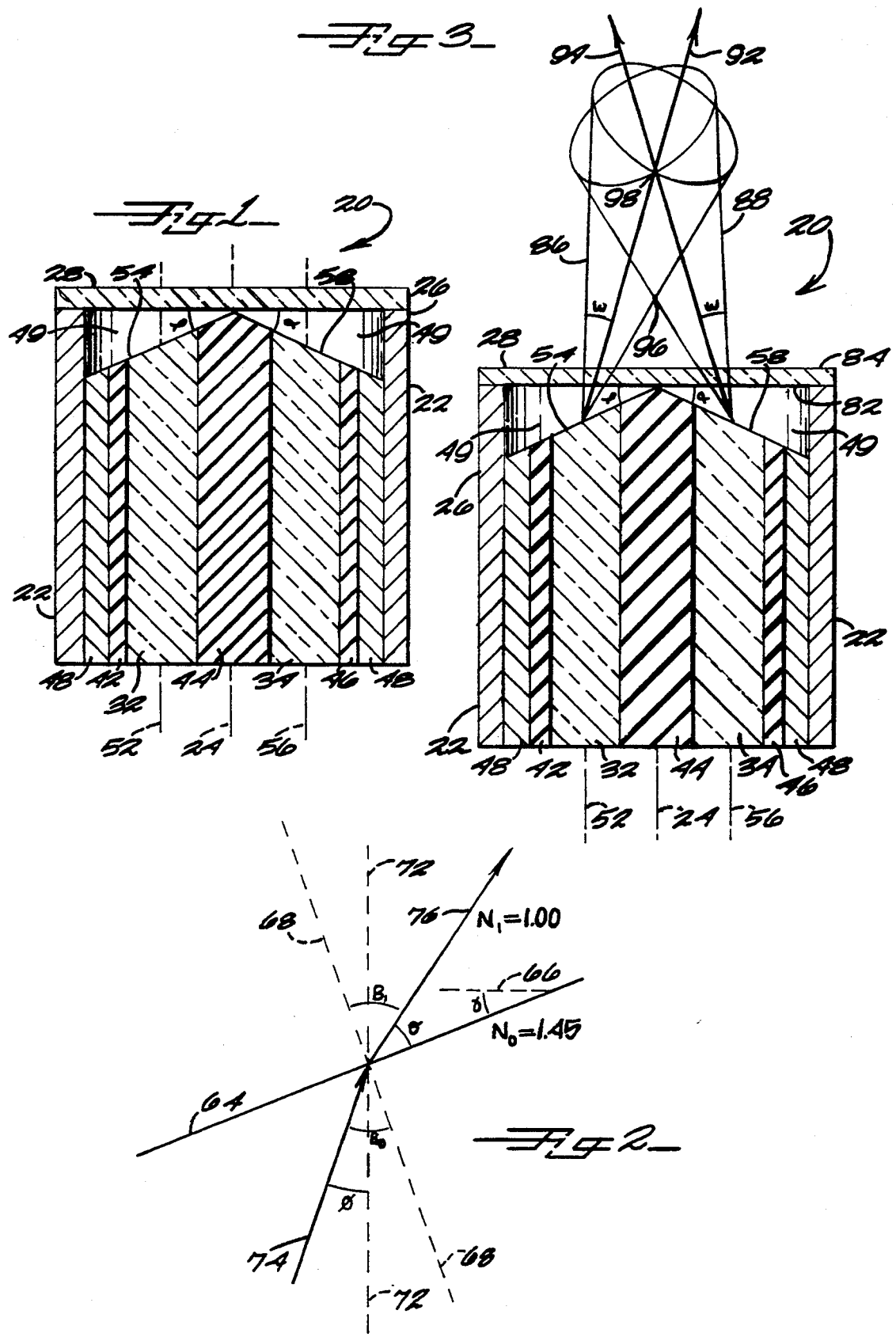

FIBER OPTIC PROBE HAVING FIBERS WITH ENDFACES FORMED FOR IMPROVED COUPLING EFFICIENCY AND METHOD USING SAME

The United States Government has rights in this invention pursuant to Contract No. DE-AC09-89SR18035 between the U.S. Department of Energy and Westinghouse Savannah River Company.

BACKGROUND OF THE INVENTION

1. Field of the Invention

The present invention relates to fiber optic probes for spectral analysis. More particularly, the present invention relates to fiber optic probes having endfaces formed for improved light coupling efficiency.

2. Discussion of Background

Fiber optic probes are known for use in the spectral analysis of samples. In a number of designs for probes, the fiber optic probe contains a source fiber and one or more receiving fibers positioned about the source fiber. Upon positioning the probe in a sample, light from the source fiber is directed through the sample to a reflecting surface, where it is reflected back to the probe and collected by the receiving fibers. Comparison of the collected light with the source light, using well known spectral analysis techniques, yields qualitative and quantitative characteristics of the sample.

Variations in fiber optic probes exist in the art to assist in spectral analysis of the sample. For instance, Yafuso et al, in U.S. Pat. No. 4,919,891, disclose an optical fiber having a protective coating surrounding the tip of the fiber. The coating, made of a cross-linked cellulosic material, is permeable to the fluid sample of interest and contains an opaque agent such as carbon black to reduce crosstalk between the fiber and other similar fibers when bundled.

Several fiber optic probes have specific fiber orientations or other directing means to enhance the receipt of light by the collecting fibers. In Kitamura et al, U.S. Pat. No. 4,816,670, an optical measuring head is disclosed having a receiving fiber, a plurality of light-projecting fibers axially disposed about the receiving fiber and a convex lens spaced apart from the ends of the fibers. The lens directs light from the projecting fibers upon a surface adjacent an object to be measured at an angle smaller than a critical angle. Light reflected from the object is focused onto the light receiving fiber.

In U.S. Pat. No. 4,914,284, Halldorsson et al disclose an optical, wide angle head for directionally sensing optical radiation. The device has a plurality of optical fibers, each having a sensor at one end. The sensors are arranged on a mounting plate so that the optical axes of each sensor pass through a common intersection point. Such arrangements are accomplished by bending the optical fibers within the optical head.

However, bending optical fibers in this manner often results in light transmission than is not as focused as if it were being transmitted out of an optical fiber in which the optic axis remains straight. Rather than orienting the receiving fibers to better collect returned light, McGee et al, in U.S. Pat. No. 5,166,756, uses a sapphire rod that abuts the ends of a plurality of optical fibers. The sapphire rod has an endface that prevents specularly reflected light from reentering the probe.

Also, fiber optic probes are known for use in scattered light detection of samples that comprise a translucent or transparent medium containing scattering particles. Such detection includes diffuse reflection, fluorescence and Raman spectroscopy. In this type of analysis, light from the source fiber passes through the sample and is partially scattered by particles having an index of refraction different than that of the sample medium. The scattered light is collected by the receiving fibers and transmitted to a detector for spectral analysis, which determines, among other things, the concentration of the particles in the sample.

Both fiber optic probes disclosed by McLachlan et al (in U.S. Pat. No. 4,707,134 and 4,573,761) have fibers, axially disposed about a central axis, that are bent toward the central axis so that the optic axes of the fibers converge. In U.S. Pat. No. 4,707,134, the probe has a plurality of fibers radially and circumferentially spaced about the axis of a cylindrical housing that is closed at one end by a transparent window. The fibers are bent so that their optic axes converge to intersect one another at a common point on the axis that is adjacent or beyond the outer surface of the window.

In U.S. Pat. No. 4,573,761, a probe used for sensitive Raman analysis is comprised of a bundle of optical fibers in which the collecting fibers are located around the circumference of the transmitting fiber. The fibers are arranged so that the ends of the collecting fibers are tilted slightly towards the center of the probe, preferably at angles less than 45 degrees.

Despite the existence of numerous fiber optic probes, there exists a need for an easily-manufacturable fiber optic probe having an improved light coupling efficiency.

SUMMARY OF THE INVENTION

According to its major aspects and broadly stated, the present invention is a fiber optic probe for detection of scattered light. In particular, it is a fiber optic probe with transmitting and receiving fibers having slanted endfaces so that when bundled form a somewhat "beveled" probe tip. The probe comprises a housing with a window across its tip for protecting the transmitting and receiving fibers. The endfaces of the fibers are slanted, by cutting, polishing and the like, so that they lie in a plane that is not perpendicular to the optic axis of the respective fiber. The fibers are held in the tip of the probe, preferably parallel to one another, using an epoxy and are oriented so that lines perpendicular to the endfaces diverge. The epoxy, which is positioned substantially between the transmitting and receiving fibers, is shaped so that the transmitting fiber, the epoxy and the receiving fiber form a bevel of not more than 20 degrees. The slanted fiber endfaces, in this preferred orientation, cause bending of the light cones emanating from the probe's transmitting fibers toward the longitudinal axis of the probe which they intersect just beyond the window, resulting in improved light coupling efficiency. Also, the epoxy is filled with a light absorber, such as carbon black, in order to reduce crosstalk between the transmitting and receiving fibers.

A major feature of the present invention is the slanting of the endfaces of the transmitting and receiving fibers so that they are not perpendicular to the optic axis of their respective fibers. The slanted endface causes light emitted from or accepted into the fiber to bend at a predetermined angle. The advantage of this feature is that fibers having slanted endfaces can be arranged easily and conveniently within the probe so that the collection of scattered light is maximized.

Another feature of the present invention is the use of an epoxy containing carbon black to absorb the light necessary to minimize optical crosstalk between the transmitting and receiving fibers. The advantage of this feature is two-fold: light collected by the receiving fiber better represents the sample being analyzed since the collected light is not littered with crosstalk; and epoxy is an easy-to-use, stable molding medium that will hold the optic fibers in the preferred arrangement.

Still another feature is the use of a thin, transparent window for defining a closed chamber between the inside of the window and the probe that can be back-filled with a gas or air having a known index of refraction so that the behavior of the light once it leaves the transmitting fibers and as it approaches the receiving fibers is as expected. The window also protects the fibers from exposure to the various samples while allowing light to pass through for emitting and collecting light information. This feature extends the life of the optical fibers in the probe while allowing for accurate light data to be obtained.

Other features and advantages of the present invention will be apparent to those skilled in the art from a careful reading of the Detailed Description of a Preferred Embodiment presented below and accompanied by the drawings.

BRIEF DESCRIPTION OF THE DRAWINGS

In the drawings,

FIG. 1 is a side cross-sectional view of a fiber optic probe according to a preferred embodiment of the present invention;

FIG. 2 is a diagrammatic view showing the effect of an optical fiber with a slanted face on light transmission in accordance with Snell's law; and FIG. 3 is a side cross-sectional view of the fiber optic probe of FIG. 1 showing the light cones of the probe fibers.

DETAILED DESCRIPTION OF A PREFERRED EMBODIMENT

In the following description, similar components are referred to by the same reference numeral in order to simplify the understanding of the sequential aspect of the drawings.

Referring now to FIG. 1, the fiber optic probe 20 in its preferred embodiment is a housing 22, having a longitudinal axis 24 and a distal end 26. A window 28 is attached across distal end 26 for protecting the contents of housing 22, which includes a transmitting fiber 32, a receiving fiber 34 and epoxy 42, 44, 46. Also, additional spacer materials such as a terminator 48 may be included to maintain the position of transmitting fiber 32, receiving fiber 34 and epoxy 42, 4, 46 within housing 22. Housing 22 is preferably a fiber optic coupling dimensioned to contain a plurality of optical fibers and made of a material suitable for repeated use in various samples.

Window 28 is a thin window made from a transparent material, preferably sapphire or silica, and is attached across distal end 26 of housing 22 so that a spacing (shown generally as 49) exists between window 28 and fibers 32, 34 and epoxy 42, 44, 46. Also, window 28 must be positioned close enough to transmitting and receiving fibers 32, 34 so that direct reflection from transmitting fiber 32 to receiving fiber 34 is avoided. The avoidance of direct reflection will be discussed more fully below.

Transmitting fiber 32 has a first optic axis 52, and a first endface 54. The endface of an optical fiber is the surface, defined by the end of the fiber, from which light exits the fiber. First endface 54 that is slanted with respect to first optic axis 52. Specifically, first endface 54 can be formed so that it lies in a plane (faceted), or a conical section (tapered), that is not perpendicular with respect to first optic axis 52. That is, first endface 54 is slanted rather than normal with respect to first optic axis 52.

Similarly, receiving fiber 34 has a second optic axis 56 and a second endface 58. Second endface 58 is slanted with respect to second optic axis 56 and lies in a plane or on a conical section not perpendicular to second optic axis 56. Preferably, first and second endfaces 54, 58 are formed by cutting, grinding, polishing (to minimize imperfections on the endface), and the like after their fixture within terminator 48 but prior to their fixture within housing 22.

Epoxy 42, 44, 46 is used for holding transmitting fiber 32 and receiving fiber 34 within distal end 26 of housing 22. Preferably, epoxy 44 is injected or otherwise positioned between transmitting and receiving fibers 32, 34 to maintain a spatial relationship therebetween. Also, epoxy (such as epoxy 42 and 46) may be positioned between transmitting and receiving fibers 32, 34 and housing 22 or terminator 48. Epoxy 42, 44, 46 adheres to the surface of transmitting and receiving fibers 32, 34 and terminator 48 to hold transmitting and receiving fibers 32, 34 within distal end 26 of housing 22.

Preferably, transmitting and receiving fibers 32, 34 are positioned within distal end 26 of housing 22 so that first and second optical axes are parallel with respect to one another and first and second endfaces 54, 58 are oriented so that lines normal to first and second endfaces 54, 58 are divergent with respect to one another, as shown. Also, epoxy 44, positioned between transmitting fiber 32 and receiving fiber 34, is preferably tapered at its distal end so that transmitting fiber 32, epoxy 44 and receiving fiber 34 form a bevel within distal end 26 of housing 22. A bevel angle, $\gamma$, is defined as shown in FIG. 1.

The slant of first endface 54 with respect to first optic axis 52 causes light transmitted from transmitting fiber 32 to pass through first endface 54 in a direction that is not normal to the plane defined by first endface 54. Thus, with transmitting fiber 32 preferably positioned as shown in FIG. 1, light transmitted from transmitting fiber 32 will be directed toward longitudinal axis 24 upon exit from transmitting fiber 32, as shown and discussed more fully below. Correspondingly, light associated with receiving fiber 34 is likewise in a direction toward longitudinal axis 24 by the same angle. Thus, transmitting and receiving fibers 32, 34 can be held parallel to each other within distal end of probe 20 yet still enjoy the benefits of having light directed toward longitudinal axis 24.

Light emitted from and accepted into transmitting and receiving fibers 32, 34 is directed toward longitudinal axis 24 by an angle defined by $(N-1)*(\gamma)$, where N is the index of refraction of the core of transmitting fiber 32, preferably 1.45. However, this is assuming that air occupies spacing 49 between transmitting and receiving fibers 32, 34 and window 28. This light-directing effect is greatly reduced if liquid occupies spacing 49, since many liquid samples generally have lo an index of refraction much closer to that of fibers 32, 34 than does air.

Referring now to FIG. 2, and in accordance with Snell's Law, a surface 64 defines a barrier between two areas: $N_1$ having an index of refraction of 1.00, and $N_0$ having an index of refraction of 1.45. Surface 64 is slanted at bevel angle $\gamma$ with respect to horizontal (shown by dashed line 66) as shown. A normal line 68 is normal to surface 64, while "true" vertical is shown by dashed line 72. Ray 74 represents the path of light being transmitted through area $N_0$; ray 76 represent the path of ray 74 once ray 74 has passed through area $N_0$ and has entered area $N_1$.

Thus, surface 64 could represent, for example, first endface 54 as shown in FIG. 1, while area $N_0$ could represent transmitting fiber 32, which preferably has an index of refraction of 1.45. Correspondingly, area $N_1$ could represent spacing 49 as shown in FIG. 1. In this manner, with area $N_0$ having an index of refraction =1.45 and area $N_1$ having an index of refraction =1.00, $N_0\sin(B_0)=N_1\sin(B_1)$ according to Snell's law.

Furthermore, $B_1$, which is the direction of light travel out of the surface 64 from normal line 68, is equal to $\text{Arcsin}(N_0/N_1\sin(B_0))$, where: $B_0$ is the angle of light ray 74 being transmitted through area $N_0$; $B_1$ is the angle of the output light ray 76 (which represents the path of ray 74 upon passing through surface 64 into area $N_1$); $N_0$ is the index of refraction of area $N_0$ and $N_1$ is the index of refraction of area $N_1$.

Also, $\cos(B_0)$=the vector product of (the ray 74 vector) and (the normal line 68 vector), with the ray 74 vector $=(\sin(\Phi)\cos(\sigma), \sin(\Phi)\sin(\sigma), \cos(\Phi))$, and the normal line 68 vector $=(\sin(\gamma), 0, \cos(\gamma))$, where: $\gamma$ is the bevel angle on surface 64 with respect to dashed line 66; $\Phi$ is the angle of ray 74 with respect to dashed line 72 and $\sigma$ is the angle of ray 76 with respect to surface 64. Since $\cos(B_0)=\sin(\gamma)\sin(\Phi)\cos(\sigma)+\cos(\gamma)\cos(\Phi)$, and $B_0=\text{Arccos}(\sin(\gamma)\sin(\Phi)\cos(\sigma)+\cos(\gamma)\cos(\Phi))$, it follows that $B_1=\text{Arcsin}(N_0/N_1\sin(\text{Arccos}(\sin(\gamma)\sin(\Phi)\cos(\sigma)+\cos(\gamma)\cos(\Phi))))$.

If it is assumed that only light rays in the plane defined by $\sigma=180$ are considered and that angles $\gamma$, $\Phi$ are small, then: $B_1=N_0/N_1(\gamma+\Phi)$, with the angle of ray 76 with respect to dashed line 72 being equal to $B_1-\gamma$, and the angle of ray 76 without bevel angle $\gamma$ being equal to $N_0/N_1(\Phi)$. Also, additional deflection from bevel angle $\gamma=((N_0/N_1)-1)*\gamma$.

Referring to FIG. 3, the characteristic light rays of transmitting fiber 32 and receiving fiber 34 are shown. As described previously and shown also in FIG. 1, transmitting and receiving fibers 32, 34 are held in housing 22 symmetrically about longitudinal axis 24 by epoxy 42, 44, 46. Window 28, which has an inner surface 82 and an outer surface 84, is attached across distal end 26 of housing 22 to enclose transmitting and receiving fibers 32, 34. Transmitting and receiving fibers 32, 34 each have an endface (first and second endfaces 54, 58, respectively) and are oriented within housing 22 so that lines normal to first and second endfaces 54, 58 are divergent with respect to one another.

Light emitted from and accepted into transmitting and receiving fibers 32, 34 falls within one of a first light cone 86 and a second light cone 88. First and second light cones 86, 88 have first and second lo central rays 92, 94, respectively. First central ray 92 and its corresponding first light cone 86 demonstrate the path of light associated with transmitting fiber 32 as a result of first endface 54 being slanted with respect to first optic axis 52. Thus, for example, light being transmitted from transmitting fiber 32 will be directed toward longitudinal axis 24, as shown by first light cone 86 and first central ray 92.

Similarly, second central ray 94 and second light cone 88 are associated with receiving fiber 34, and are directed toward longitudinal axis 24 as a result of second endface 58 being slanted with respect to second optic axis 56. Thus, for example, light received most effectively by receiving fiber 34 will be comprised of light contained within second light cone 88.

First light cone 86 and second light cone 88 intersect at a minimum crossing point 96. Similarly, first central ray 92 and second central ray 94 intersect at an optimum crossing point 98. The positioning of window 28 with respect to minimum crossing point 96 affects the efficiency of probe 20.

To measure solid or gaseous samples, probe 20 must be constructed so that inner and outer surfaces 82, 84 of window 28 are positioned between minimum crossing point 96 and transmitting and receiving fibers 32, 34. That is, window 28 must be closer to transmitting and receiving fibers 32, 34 than minimum crossing point 96. If window 28 is positioned outside of minimum crossing point 96, a portion of the light from transmitting fiber 32 will be reflected directly from transmitting fiber 32 to receiving fiber 34 without interacting with the sample.

Alternatively, liquid samples generally have an index of refraction close to that of window 28, thus outer surface 84 of window 28 does not reflect much light back to receiving fiber 34. Therefore, when used for measuring liquid samples, probe 20 can be constructed so that window 28 is substantially thicker than when probe 20 is used for gaseous samples and solid samples.

Regardless of the type of sample being used, probe 20 should be constructed so that the thickness of window 28 is such that outer surface 84 is just short of optimum crossing point 98, since optimum crossing point 98 represents the optimum distance from the tip of probe 20 to a highly scattering sample. The derivation for the distances of minimum crossing point 96 and optimum crossing point 98 is shown below. These distances should be adjusted for the thickness of window 28 by adding: (((window thickness)×(window index of refraction - 1))/(window index of refraction)).

Assuming that transmitting fiber 32 and receiving fiber 34 each have radius R and are held symmetrically about longitudinal axis 24, first and second light cones 86, 88 each have a half angle w, as shown in FIG. 3. Because endfaces 54, 58 are slanted to form a bevel (with bevel angle $\gamma$), first and second light cones 86, 88 are tilted toward each other by the angle $((N_0/N_1)-1*\gamma)$.

As stated previously, optimum crossing point 98 is the point where first and second central rays 92, 94 cross and is the optimum distance for sample placement. Assuming that $N_1=1.00$ (air) and $N_0=N$, optimum crossing point 98 is equal to $R*(1/\tan((N-1)*\gamma)-\tan(\gamma))$. With window 28 in front of probe 20, optimum crossing point 98 is extended by: (Thickness of window 28)*$(N_w-1)/N_w$, where $N_w$ is the index of refraction of window 28.

Minimum crossing point 96 is the first point where extreme rays from first and second light cones 86, 88 cross and is the minimum distance at which light from one of transmitting and receiving fibers 32, 34 can scatter into the other. Minimum crossing point 96 is equal to $R*(1/\tan((N-1)*\gamma+w)-\tan(\gamma))$.

Preferably, first and second endfaces 54, 58 form a bevel having bevel angle $\gamma$ of approximately 20 degrees.

If bevel angle γ is greater than approximately 20 degrees, or if there are imperfections in the finish of first and second endfaces 54, 58, light from transmitting fiber 32 can be reflected directly into receiving fiber 34.

This direct reflection, commonly called optical crosstalk, is particularly noticeable when using lasers as the source for light in transmitting fiber 32. To prevent optical crosstalk between transmitting and receiving fibers 32, 34, epoxy 44 is spiked with a light absorber, such as carbon black. The light absorber is very effective in preventing direct coupling of light from one of transmitting and receiving fibers 32, 34 to the other.

In use, probe 20 is positioned adjacent to a sample (not shown) that contains a plurality of particles that scatter light. Probe 20 is positioned in the sample so that window 28 and quite possibly distal end 26 of housing 22 is immersed in the sample.

Light transmitted through transmitting fiber 32 is directed through spacing 49, window 28 and into the sample substantially in the form of first light cone 86. As described above, first light cone 86 is directed toward longitudinal axis 24 as the result of the slant of first endface 54 with respect to first optic axis 52.

The presence of light scattering particles in the sample causes a portion of the light transmitted into the sample to be scattered and, to a certain extent, scattered back toward window 28, thereby being made available for collection. The scatter light within what is shown in FIG. 2 as second light cone 88 is collected by receiving fiber 34 for analysis.

Besides detection of scattered light, probe 20 can be used in other spectral analysis where it is beneficial to have light cones directed toward a central axis for more efficient light transmission and collection. By using optical fibers having slanted tips, probe 20 can have bundled fibers in parallel within probe 20 without sacrificing light coupling efficiency. Thus, probe 20 is much easier to fabricate and maintain operability than fiber optic probes with fibers bent toward one another or probes that use lens systems to direct transmitted and collected light.

It will be apparent to those skilled in the art that many changes and substitutions can be made to the preferred embodiment herein described without departing from the spirit and scope of the present invention as defined by the appended claims.

What is claimed is:

1. A fiber optic probe, said probe comprising:
   a first fiber having a first axis and a first endface, said first endface formed so that light passing through said first endface passes through said first endface at an angle less than perpendicular with respect to said first endface;
   a second fiber having a second axis and a second endface, said second fiber in optical communication with said first fiber so that when a light scattering means is positioned within a range beyond said first and second endfaces, a portion of light transmitted by one of said first and second fibers is reflected by said light scattering means and substantially collected by the other of said first and second fibers: and
   means for holding said first and second fibers in optical communication, said holding means having an epoxy positioned between and adhering to said first and second fibers, said epoxy containing a light absorber to minimize crosstalk between said first and second fibers.

2. The probe as recited in claim 1, wherein said second endface lies along a conical section that is not perpendicular with respect to said second axis.

3. The probe as recited in claim 1, wherein said first endface lies along a conical section that is not perpendicular with respect to said first axis.

4. The probe as recited in claim 1, wherein said probe has a distal end and wherein said probe further comprises means for holding said first and second fibers in spaced relation within said distal end so that said first and second fibers are in optical communication.

5. The probe as recited in claim 1, wherein said first endface lies along a conical section that is not perpendicular with respect to said first axis, wherein said second endface lies along a conical section that is not perpendicular with respect to said second axis, and wherein said probe further comprises means for holding said first and second fibers in spaced relation so that said first and second axes am parallel with respect to one another and said first and second endfaces are divergent from one another.

6. The probe as recited in claim 1, wherein said probe has a longitudinal axis and wherein said first fiber is oriented within said probe so that light passing through said first endface is directed toward said longitudinal axis.

7. The probe as recited in claim 1, wherein said first endface lies along a conical section that is not perpendicular with respect to said first axis, wherein said second endface lies along a conical section that is not perpendicular with respect to said second axis, and wherein said probe further comprises means positioned between said first and second fibers for holding said first and second fibers in spaced relation so that said first and second axes are parallel with respect to one another, said holding means having a tapered tip so that said first endface, said holding means and said second endface form a bevel having an angle of less than approximately 20 degrees.

8. The probe as recited in claim 1, wherein each of said first and second endfaces is formed by a method comprising the steps of:
   cutting said endface at an angle that is not perpendicular to said axis so that said endface lies along a conical section that is not perpendicular with respect to said axis; and
   polishing said endface.

9. A fiber optic probe, said probe having a longitudinal axis, said probe comprising:
   at least one transmitting fiber having a first optic axis and a first endface, said first endface formed so that light passing through said first endface passes through said first endface at an angle less than perpendicular with respect to said first endface, said transmitting fiber oriented so that light passing through said first endface is directed toward said longitudinal axis;
   at least one receiving fiber having a second optic axis and a second endface, said second endface formed so that light passing through said second endface passes through said second endface at an angle less than perpendicular with respect to said second endface, said receiving fiber oriented so that light passing through said second endface is directed toward said longitudinal axis; and
   means for holding said transmitting and receiving fibers in spaced relation so that said first and second optic axes are parallel with respect to one another, said holding means holding said transmitting and receiving fibers so that when a light scattering means is positioned within a range beyond said first and second endfaces, a portion of light transmitted from said transmitting fiber is reflected by said light scattering means and substantially collected by said receiving fiber, said holding means having an epoxy positioned between and adhering to said transmitting and receiving fibers, said epoxy containing a light absorber to minimize crosstalk between said transmitting and receiving fibers.

10. The probe as recited in claim 9, wherein said first endface lies along a conical section that is not perpendicular with respect to said first optic axis and said second endface lies along a conical section that is not perpendicular with respect to said second optic axis.

11. The probe as recited in claim 9, wherein said first endface lies along a conical section that is not perpendicular with respect to said first optic axis and said second endface lies along a conical section that is not perpendicular with respect to said second optic axis and wherein said holding means holds said transmitting and receiving fibers so that said first and second endfaces are divergent with respect to one another.

12. The probe as recited in claim 9, further comprising a window attached to said distal end for enclosing said distal end, said window positioned just beyond said first and second endfaces and maintaining a constant environment therebetween.

13. The probe as recited in claim 9, wherein said holding means further comprises:
 a housing having a distal end for carrying said transmitting and receiving fibers therein; and
 said epoxy adhering to said transmitting fiber, said receiving fiber and said housing so that said transmitting and receiving fibers are held in spaced relation within said distal end of said housing.

14. The probe as recited in claim 9, wherein said holding means is tapered so that said first endface, said holding means and said second endface form a bevel having an angle of less than approximately 20 degrees.

15. A method for increasing the light coupling efficiency of a fiber optic probe, said probe having a distal end and a longitudinal axis, said method comprising the steps of:
 forming a first endface on a first fiber so that light passing through said first endface passes through said first endface at an angle less than perpendicular with respect to said first endface, said first fiber carried in said distal end of said probe, said first fiber having a first optic axis;
 forming a second endface on a second fiber so that light passing through said second endface passes through said second endface at an angle less than perpendicular with respect to said second endface, said second fiber carried in said distal end of said probe, said second fiber having a second optic axis;
 aligning said first and second fibers so that first and second optic axes are parallel;
 axially orienting said first and second fibers so that when a light scattering means is positioned within a range beyond said first and second endfaces, a portion of light transmitted by one of said first and second fibers is reflected by said light scattering means and substantially collected by the other of said first and second fibers; and
 inserting an epoxy in said distal end of said probe, said epoxy adhering to said first fiber, said second fiber and said distal end so that said first and second fibers are held in said distal end, said epoxy containing a light absorber to minimize crosstalk between said first and second fibers.

16. The method as recited in claim 15, further comprising the step of:
 attaching a window to said distal end of said probe to enclose said first and second fibers within said probe, said window positioned just beyond said first and second endfaces and maintaining a constant environment therebetween.

17. The method as recited in claim 15, wherein each of said first and second forming steps further comprise the steps of:
 cutting said endface at an angle that is not perpendicular with said axis so that said endface lies along a conical section that is not perpendicular with said axis, and
 polishing said endface to remove any imperfections existing on said endface.

* * * * *